US00PP37550P3

(12) United States Plant Patent
Grosser

(10) Patent No.: US PP37,550 P3
(45) Date of Patent: Aug. 4, 2026

(54) SWEET ORANGE PLANT NAMED 'N14-10'

(50) Latin Name: *Citrus sinensis*
Varietal Denomination: N14-10

(71) Applicant: Florida Foundation Seed Producers, Inc., Marianna, FL (US)

(72) Inventor: Jude Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 19/381,419

(22) Filed: Nov. 6, 2025

(65) Prior Publication Data

US 2026/0130300 P1 May 7, 2026

Related U.S. Application Data

(60) Provisional application No. 63/717,509, filed on Nov. 7, 2024.

(51) Int. Cl.
*A01H 5/08* (2018.01)
*A01H 5/02* (2018.01)
*A01H 6/78* (2018.01)

(52) U.S. Cl.
USPC ..... Plt./202
CPC ..... *A01H 6/785* (2018.05); *A01H 5/02* (2013.01); *A01H 5/08* (2013.01)

(58) Field of Classification Search
USPC ..... Plt./156, 201, 202
See application file for complete search history.

(56) References Cited

U.S. PATENT DOCUMENTS

PP27,145 P3 9/2016 Grosser
PP27,744 P3 3/2017 Grosser

*Primary Examiner* — Susan Mccormick Ewoldt
(74) *Attorney, Agent, or Firm* — Koenig IP Works, PLLC; Katherine Koenig

(57) ABSTRACT

A new and distinct cultivar of sweet orange plant named 'N14-10', characterized by a high brix and increased dissolved solids.

12 Drawing Sheets

Genus and species: *Citrus sinensis.*
Cultivar denomination: 'N14-10'.

BACKGROUND OF THE NEW CULTIVAR

The present invention relates to a new and distinct cultivar of 'Hamlin' sweet orange, botanically known as *Citrus sinensis,* and hereinafter referred to by the name 'N14-10'. *Citrus sinensis* is a member of Rutaceae.

The new sweet orange cultivar 'N14-10' is a somaclone (protoclone) regenerated from protoplasts isolated from an embryogenic suspension culture of standard 'Hamlin' (*Citrus sinensis* L. Osbeck) in 1989 (see Jude W. Grosser and Frederick G. Gmitter Jr., "Protoplast Fusion and Citrus Improvement," Plant Breeding Reviews 8:339-374 (1990) for methodology), the entirety of which is incorporated herein by reference). Somaclonal variation is defined as variability in plants regenerated from tissue culture that is either induced or uncovered by a tissue culture process. Most somaclonal variation is negative, but if enough plants are examined, positive changes can usually be recovered. Somaclonal variation has been a primary source of genetic variation in sweet orange exploited in our citrus improvement program. The new cultivar 'N14-10' is the second of three superior 'Hamlin' somaclones selected for release from more than 500 somaclones evaluated. The original tree, grafted to 'Swingle' citrumelo rootstock (commercial cultivar, not patented), was planted in Lake Alfred, Florida, in 1991. The only existing second-generation trees are on 'UFR-3' (US Plant Pat. No. 27,744) rootstock planted in 2017 in Lake Alfred, Florida. Recently, clean budwood became available in the Florida Parent Tree Program (PTP), a program through which citrus trees are selected and propagated for commercial release.

A sweet orange cultivar 'N13-32' (US Plant Pat. No. 27,145) was one of three original 'Hamlin' somaclones selected for improved juice quality, including juice color, brix and soluble solids, based on several years of juice quality data (Table 1). Selection of improved 'Hamlin' clones has proven to be quite difficult due to extreme variability in clonal juice quality data from year to year (unlike 'Valencia'; commercial cultivar, not patented). Improved brix and soluble solids of 'N14-10' was noticed during the first two years of fruiting (1995-1996). Among the hundreds of 'Hamlin' clones evaluated, 'N14-10' was always among the top clones for high brix, and it usually had the highest brix. The consistent production of higher brix juice makes this clone stand out. The current HLB-induced brix crisis in standard 'Hamlin' across the industry in the past two seasons has generated interest in this clone. Because of its ability to produce fruit with higher brix, it was also chosen for rapid budwood scaleup by the Department of Plant Industry (DPI) of the Florida Department of Agriculture & Consumer Services (FDACS).

SUMMARY OF THE INVENTION

The new sweet orange cultivar 'N14-10' has not been observed under all possible environmental conditions. The phenotype of the new cultivar may vary with variations in environment and cultural practices such as temperature, light intensity, fertilization, irrigation, and application of plant growth regulators without any change in genotype.

The new cultivar 'N14-10' is an early season clone of 'Hamlin' sweet orange (not patented) with higher brix and better soluble solids for processing.

All fruit quality data on 'N14-10' are from trees growing on either 'Swingle' citrumelo or 'UFR-3' rootstocks. No information is available on how this selection will perform on other rootstocks. Although no formal yield data is available, yearly observations on both the first and second generation trees indicate that 'N14-10' produces yields that are like those typical for 'Hamlin', with alternate bearing being less on the second generation trees than the first generation tree. Two replicated commercial field trials established to obtain formal yield data were destroyed prior to the generation of yield data due to excessive disease impact.

The new cultivar 'N14-10' can be compared to the commercial cultivar 'N13-32' (US Plant Pat. No. 27,145), a 'Hamlin' cultivar, in that fruit of the new cultivar 'N14-10' matures earlier and has higher brix and soluble solids. Additionally, trees of 'N14-10' come into bearing one year faster than those of 'N13-32'. The new cultivar 'N14-10' also has higher brix and soluble solids than the most widely planted commercial Hamlin cultivar '1-4-1'.

DESCRIPTION OF THE FIGURES

This new sweet orange cultivar 'N14-10' is illustrated by the accompanying photographs which show the tree's from, foliage and fruit. The colors shown are as true as can be reasonably obtained by conventional photographic procedures. The photographs are of a tree being approximately 7 years old.

FIG. 5 shows a typical 'Hamlin' cropping of immature fruit growing on seven-year-old tree of the new cultivar 'N14-10' at;

DETAILED BOTANICAL DESCRIPTION OF THE CULTIVAR

Figure 1:
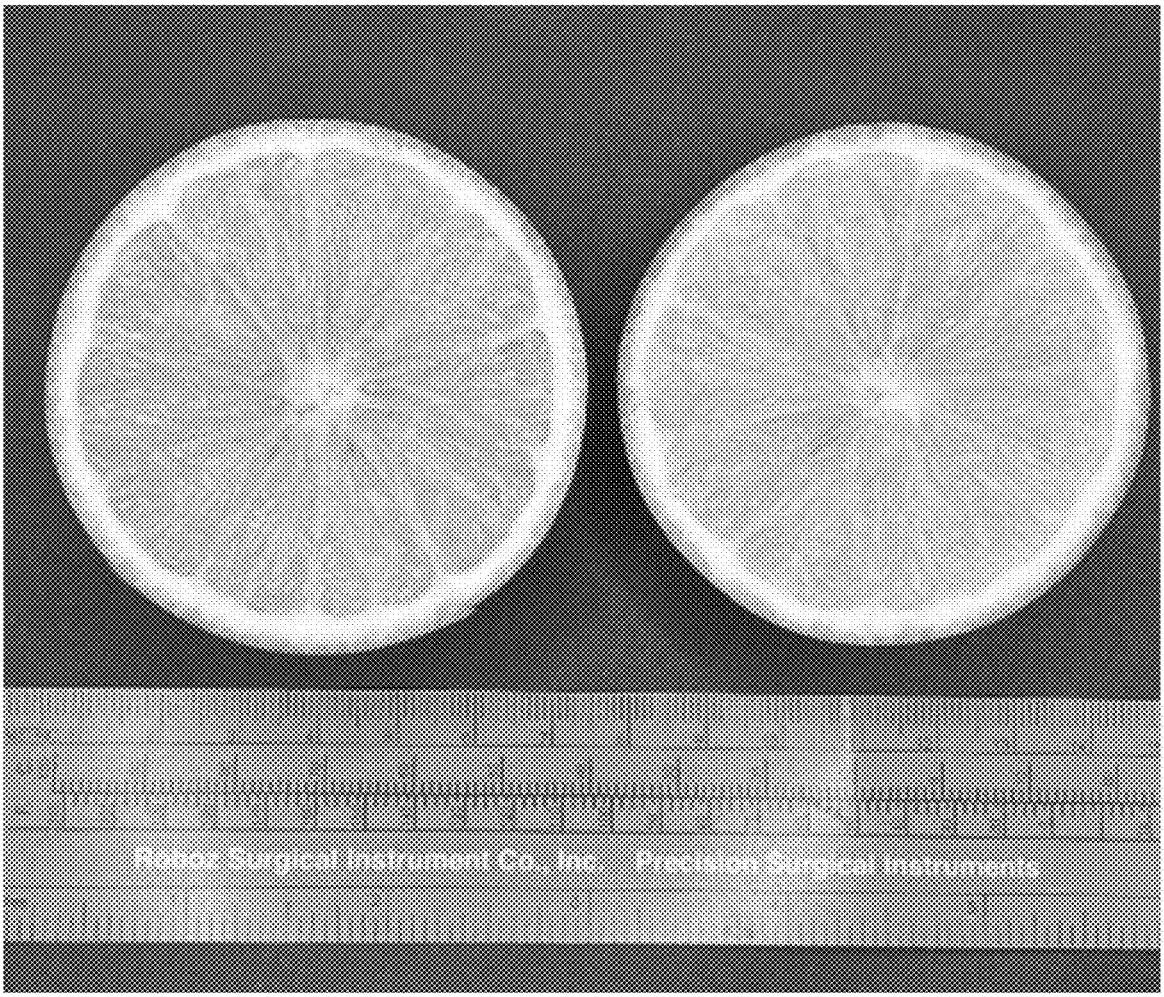
FIG. 1 shows a close-up view of cut fruit of the new cultivar 'N14-10'.
Figure 2:
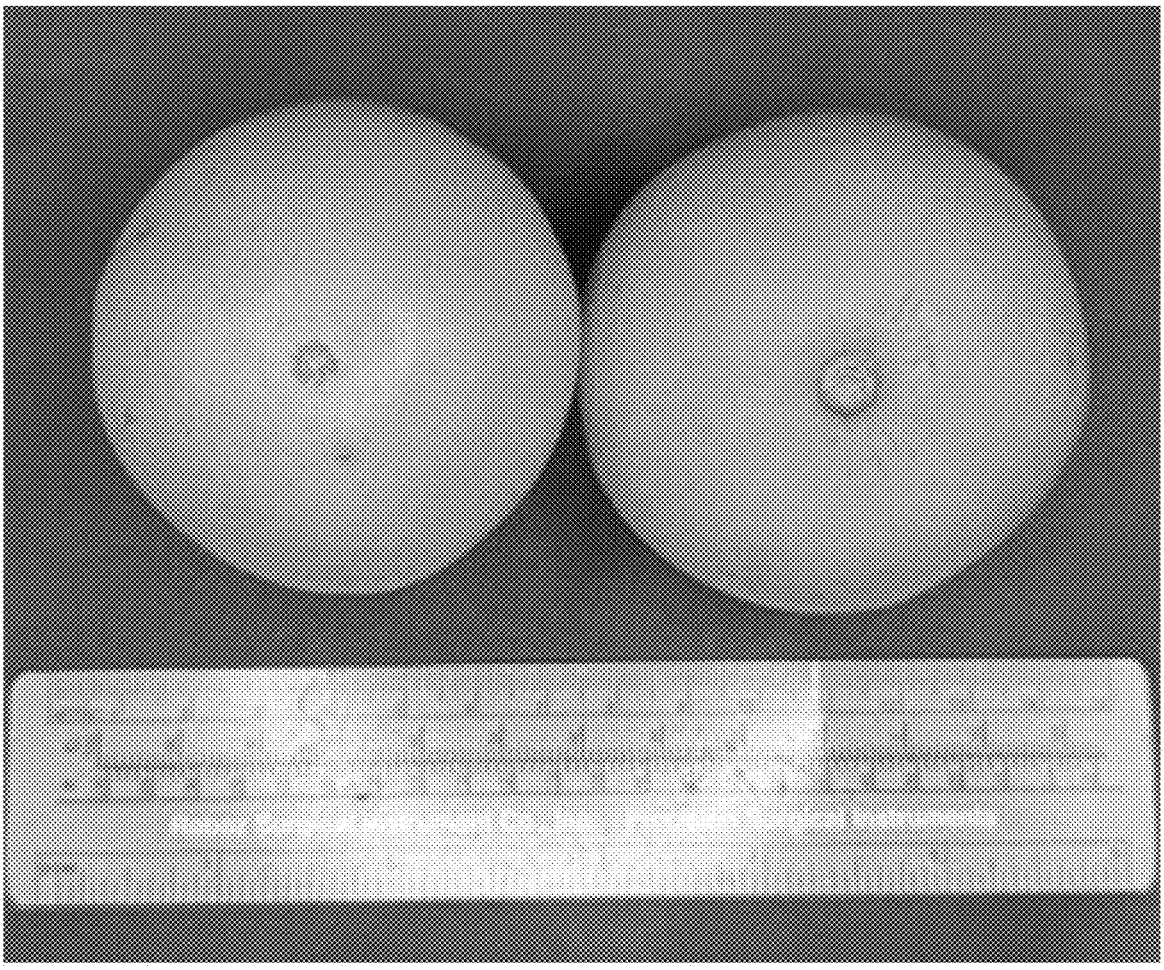
FIG. 2 shows both ends (stylar and stem) of the fruit of the new cultivar 'N14-10' with a ruler shown for size reference.
Figure 3:
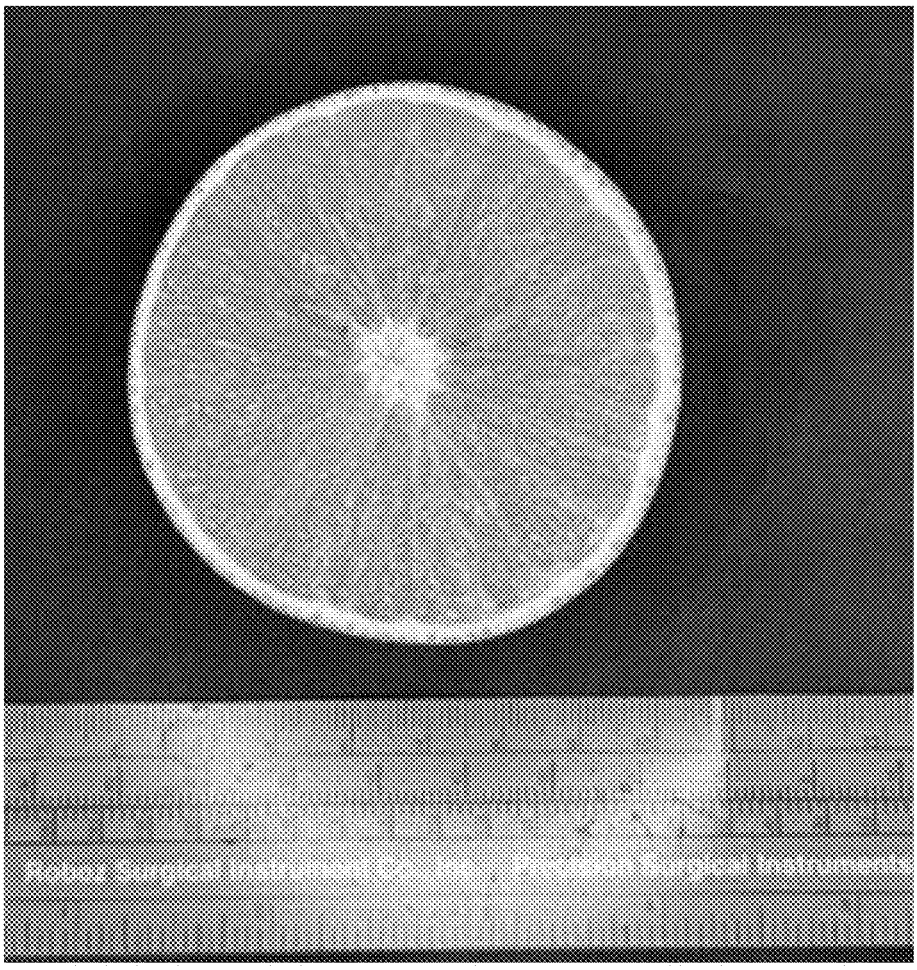
FIG. 3 shows a close-up view of cut fruit of the new cultivar 'N14-10' with a ruler shown for size reference.
Figure 4:
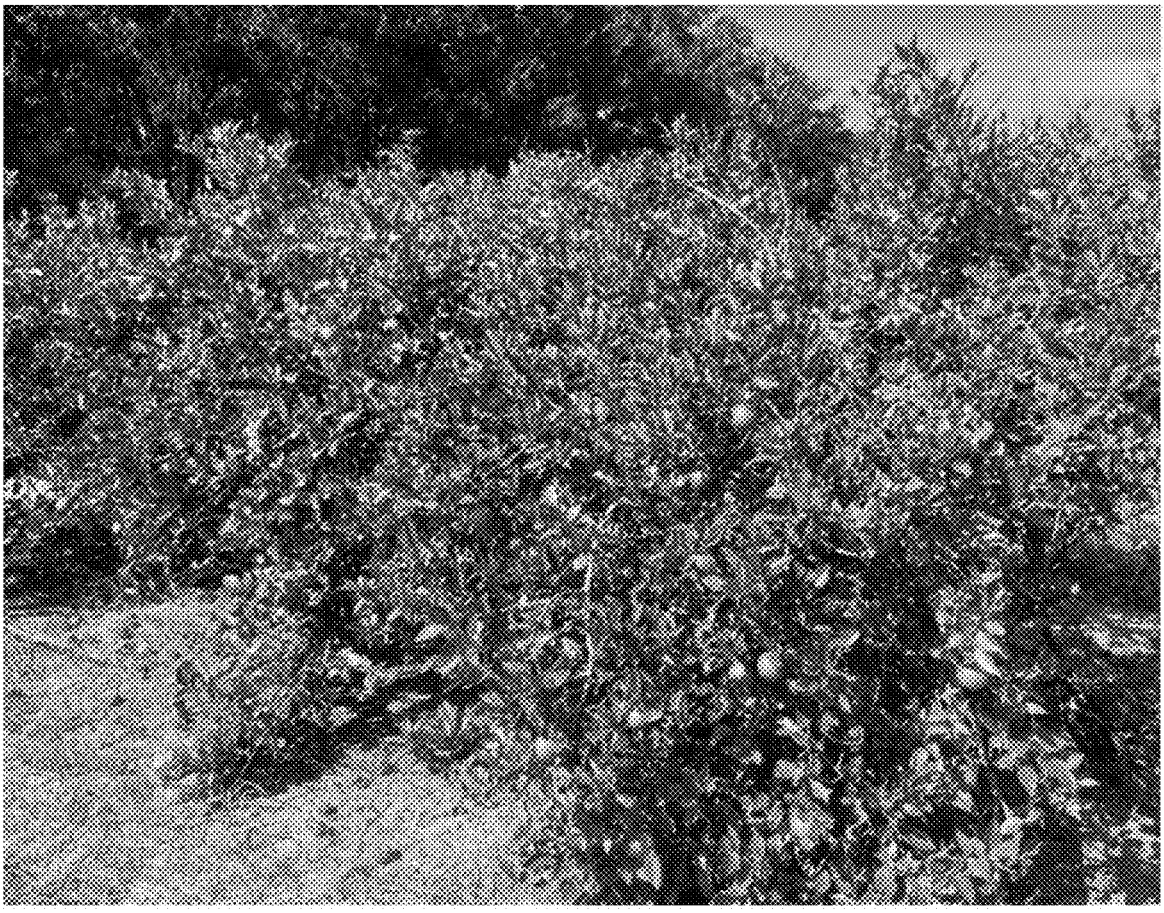
FIG. 4 shows a seven-year-old tree of the new cultivar 'N14-10' in a grove in Florida (July 2024)
Figure 5:
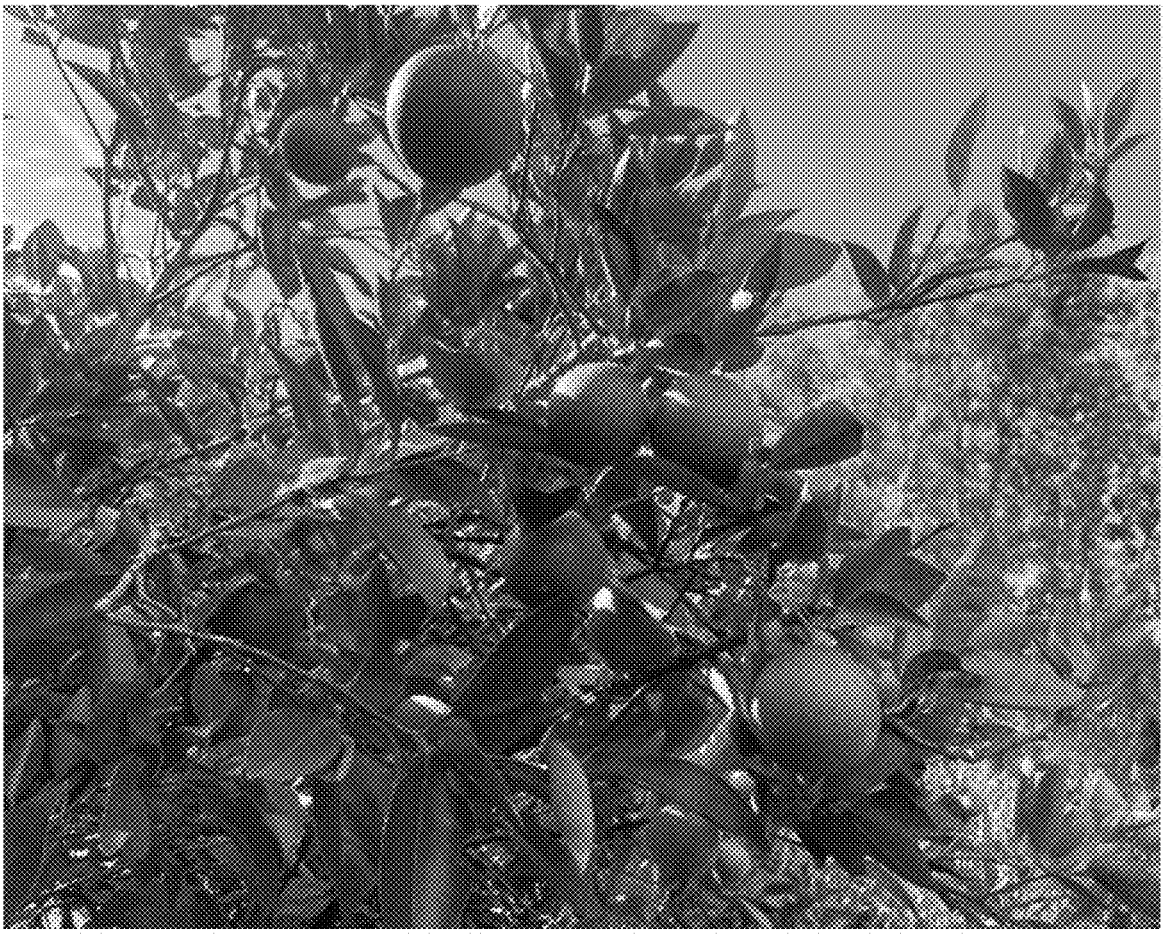
Figure 6:
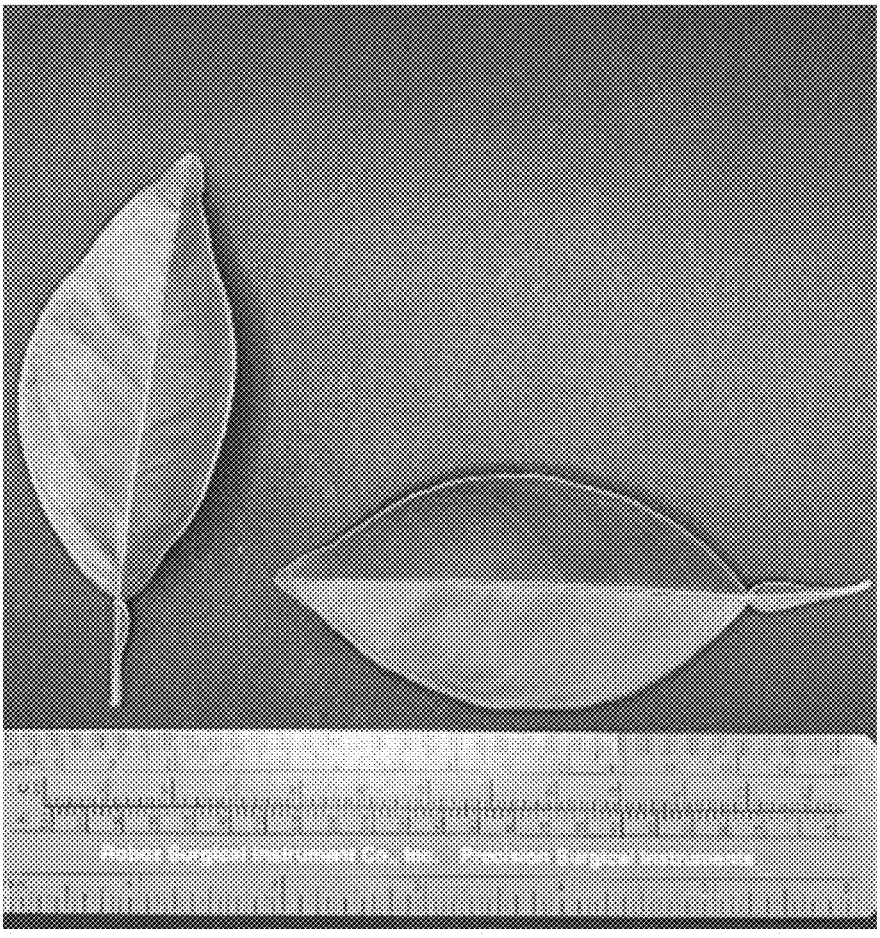
FIG. 6 shows fully expanded leaves of the new cultivar 'N14-10' with a ruler for size estimates.
Figure 7:
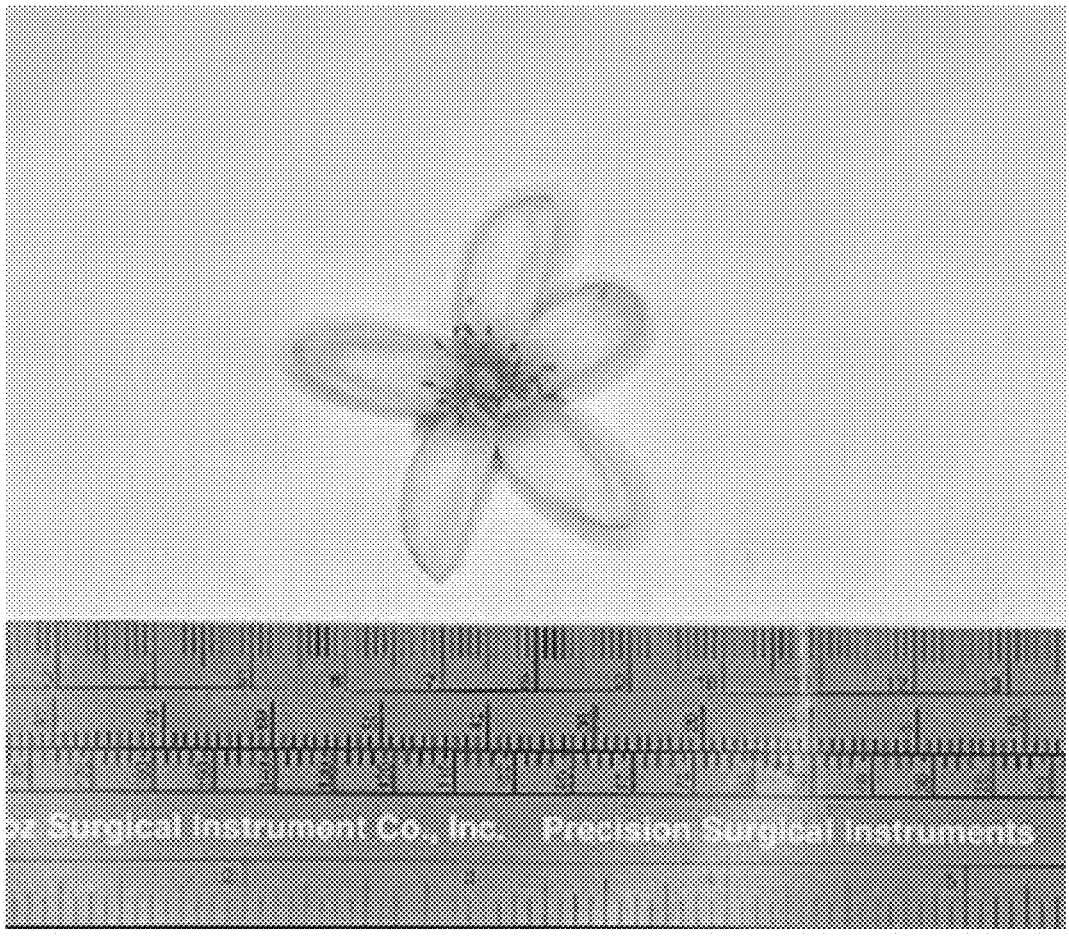
FIG. 7 shows a close-up view of a fully expended flower of the new cultivar 'N14-10' with a ruler for size reference.
Figure 8:
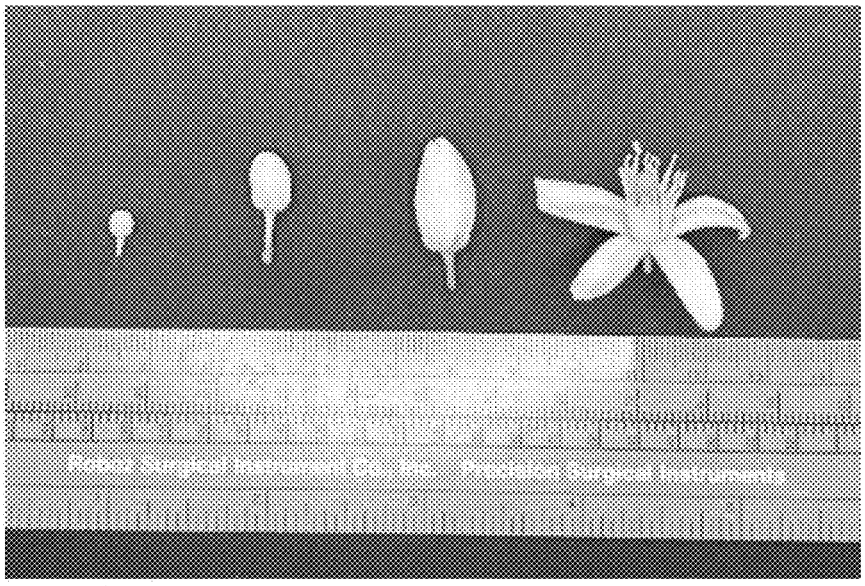
FIG. 8 shows different growth stages of flowers of the new cultivar 'N14-10' with a rule for size reference.
Figure 9:
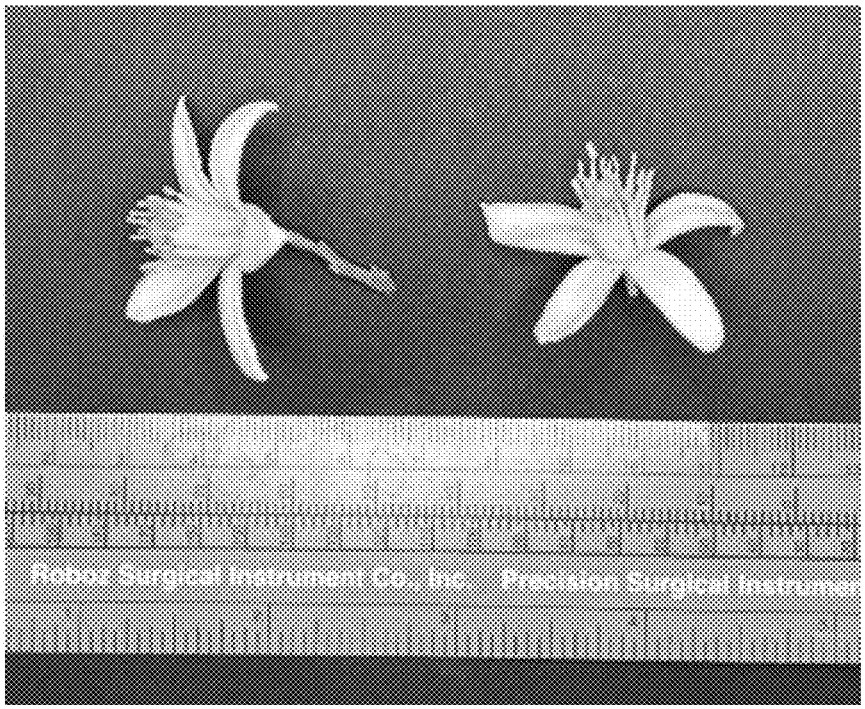
FIG. 9 shows flower diameter and flower depth of flowers of the new cultivar 'N14-10' with a ruler for size reference.
Figure 10:
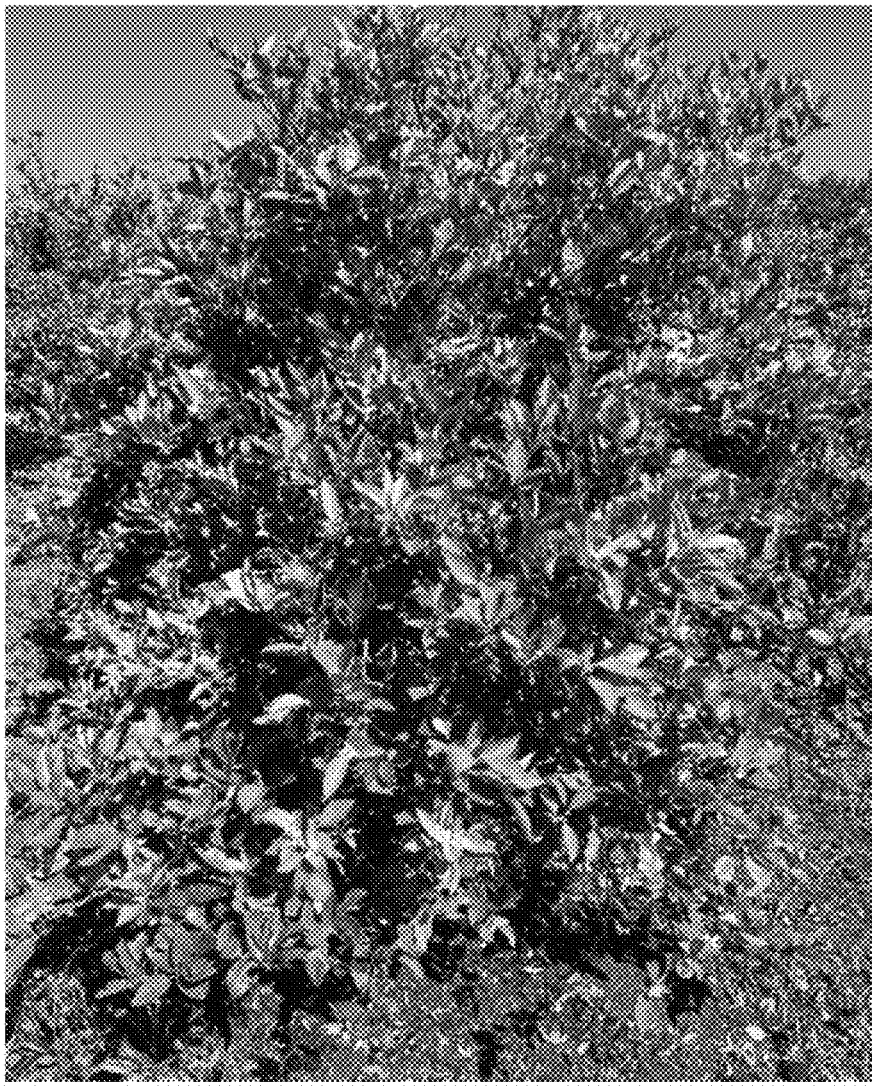
FIG. 10 shows overall tree growth habit of the new cultivar 'N14-10' in a 7-year-old tree.
Figure 11:
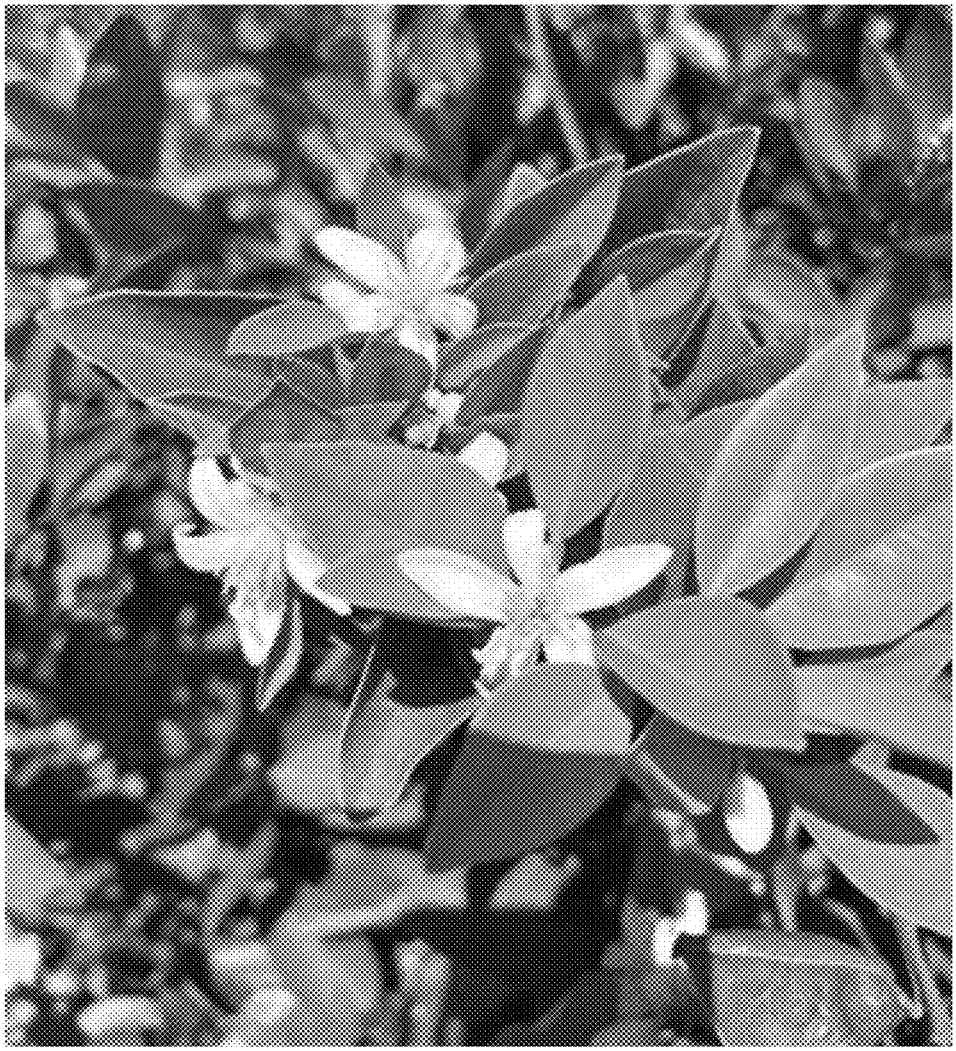
FIG. 11 shows a cluster with flowers of the new cultivar 'N14-10'.
Figure 12:
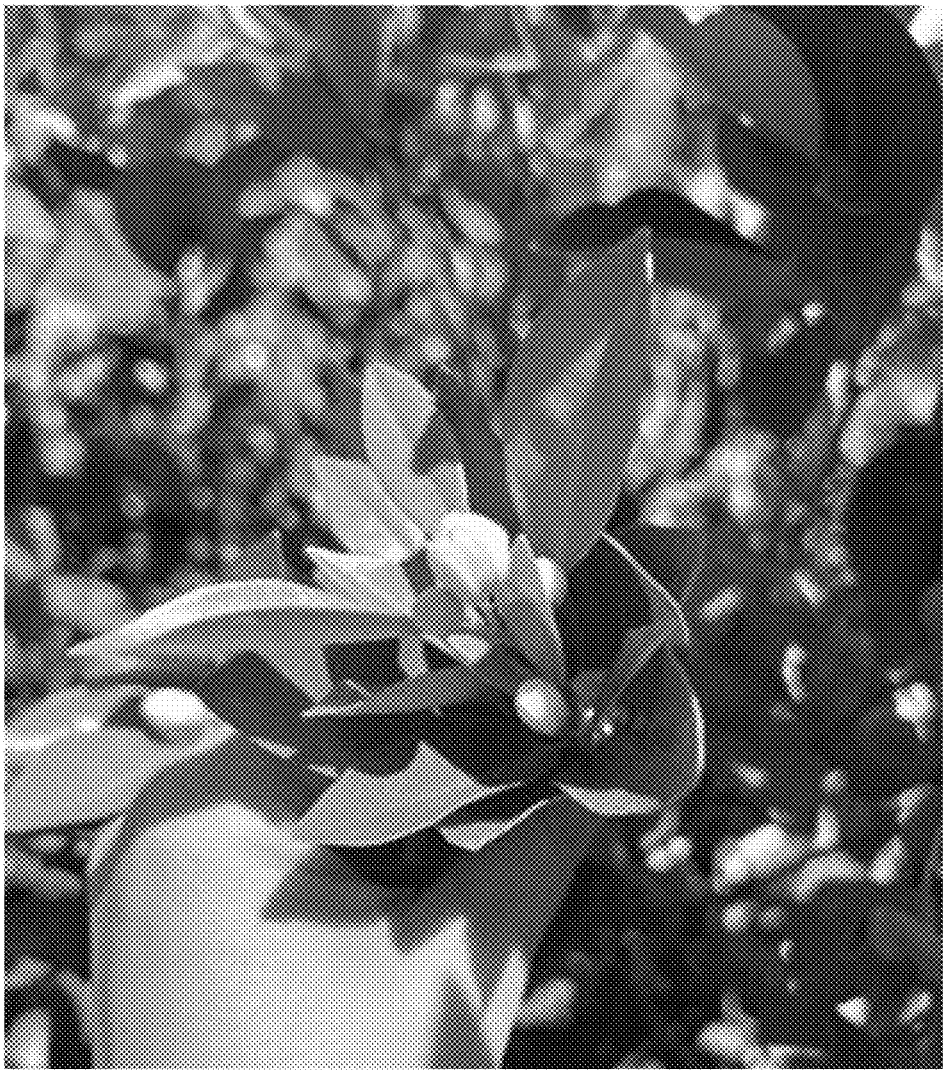
FIG. 12 shows cluster with flower buds of the new cultivar 'N14-10' in different growth stages.
Figure 13:
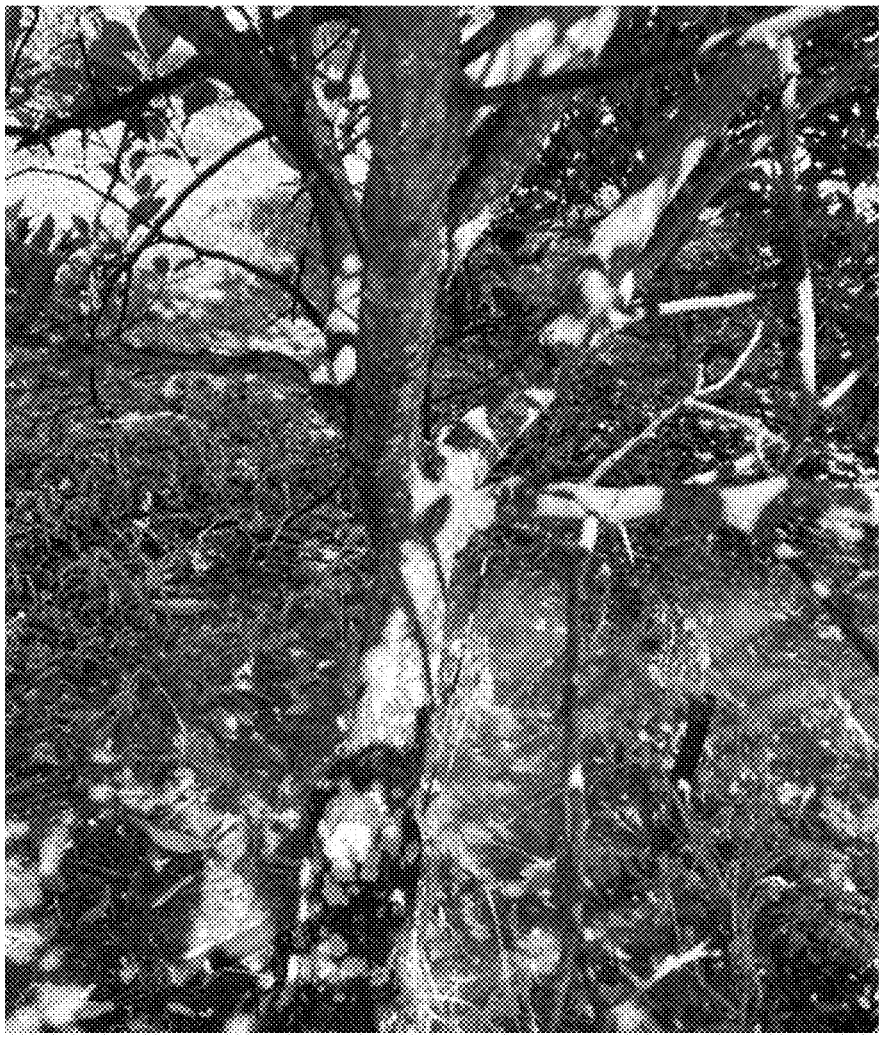
FIG. 13 shows trunk and branches of a 7-year-old tree of the new cultivar 'N14-10'.

The colors (except those in common terms) are described from R. H. S. Colour Chart published by The Royal Horticultural Society in London (2007, 5th edition), in association with the Flower Council of Holland.

Background

The new cultivar 'N14-10' is a somaclone (protoclone regenerated from embryogenic suspension culture protoplasts) of standard 'Hamlin' sweet orange.

Botanical Description

Botanical classification:
- *Family*.—Rutaceae.
- *Botanical name*.—*Citrus sinensis*.
- *Common name*.—Sweet orange.
- *Cultivar*.—'N14-10'.

Parentage: 'Hamlin' sweet orange.

Tree:
- *Ploidy*.—Diploid.
- *Size*.—Medium.
- *Width across the row*.—Approximately 2.8 meters.
- *Width down the row*.—Approximately 2.74 meters.
- *Tree height*.—Approximately 3.35 meters.
- *Tree canopy diameter*.—Approximately 9.93 meters.
- *Vigor*.—High.
- *Density*.—High.
- *Tree shape* (*form*).—Round shaped.
- *Growth habit* (*current season*).—Rounded.
- *Trunk*.—Trunk diameter: Approximately 24 cm at 30 cm above the ground. Trunk texture: Rough. Trunk bark color: RHS 197C (Greyed Green Group).
- *Branches*.—Branch length: 1.5 meters on average. Branch diameter: 13 cm on average. Crotch angle: On average, the angle is less than 90 degrees in the middle of the tree and some crotch angles on the outside are more than 90 degrees. Branch texture: Less rough than the trunk. Branch color: RHS 201A (Grey Group).

Leaves:
- *Size* (*lamina average*).—Length: 110.4 mm on average. Width: 53.2 mm on average. Thickness: Relatively thick (approximately 0.2 mm). Type: Simple (unifoliate). Shape: Elliptical. Apex: Acute. Base: Acute. Margin: Entire with a smooth lobe.
- *Surface*.—Upper surface: Smooth. Lower surface: Smooth.
- *Color*.—Upper surface (adaxial): RHS 137B (Green Group). Lower surface (abaxial): RHS 146C (Yellow-Green Group).
- *Petiole*.—Shape and attachment: Brevipetiolate. The junction between petiole and lamina is articulate. Shape (petiole wing): Small and narrow. Length: 21.3 mm on average. Width: 1.1 mm on average. Color: RHS 145A (Yellow-Green Group).

Flowers:
- *Type*.—Hermaphrodite.
- *Flowers bearing*.—Single or cluster, with each cluster having around 5 flowers. Some flowers can grow individually.
- *Flower diameter*.—41.6 mm on average.
- *Flower depth*.—14 mm on average.
- *Flower blooming period*.—Typically March.
- *First bloom*.—February.
- *Full bloom*.—March.
- *Fragrance*.—Fragrant.
- *Length*.—1.1 mm on average for the initially visible flower bud; 15 mm on average for the mature flower buds before opening.

*Diameter*.—1 mm on average in the initial visible flower bud; 6 mm on average in the matured bud.

*Flower bud shape*.—Round shape.

*Flower bud color*.—RHS 144C (Yellow-Green Group) for the initial visible flower bud; RHS 155B (White Group) for mature buds.

*Fertility*.—Appears to be self-fertile.

*Petals*.—Number: Most with 5 petals, but some with 4 petals. Petal length: 19.4 mm on average. Petal width: 7.2 mm on average. Petal shape: Recurved/cruciform. Apex shape: Smooth with an obtuse angle. Base shape: Obtuse.

*Petal color*.—Upper Surface: RHS 158D (Yellow-White Group). Lower surface: RHS 157D (Green-White Group). Margin: Smooth.

*Sepal*.—Number (per flower): Between 4 and 6. Shape: Recurved/cruciform. Length: 3.6 mm on average. Width: 3.7 mm on average. Apex shape: Smooth with an obtuse angle. Margin: Obtuse.

*Sepal color*.—Upper surface: RHS N144A (Yellow-green Group). Lower surface: RHS N145D (Yellow-green Group).

*Pedicel*.—Length: 7.4 mm on average. Diameter: 1.8 mm on average. Color: RHS 154D (Yellow-green Group).

*Stamen*.—Number: 22-23 per flower on average. Length: 11.4 mm on average.

*Anther*.—Length: 0.8 mm on average. Width: 0.5 mm on average. Color: RHS 14A (Yellow Orange Group). Pollen color (general): RHS 162A (Greyed-Yellow Group).

*Pistil*.—Number: 1. Length: 12.9 mm on average. Color: RHS 150D (Yellow-Green Group). Style length: 8.6 mm on average. Style diameter: 1.3 mm on average. Style color RHS: RHS 150D (Yellow-Green Group). Ovary shape: Oval. Ovary diameter: 3.2 mm on average. Ovary color: RHS 154 (Yellow Green Group).

Fruit:

*Size*.—Medium.

*Average weight* (*per individual fruit*).—135 grams.

*Length* (*height*).—53 mm on average.

*Diameter*.—65 mm on average.

*Shape*.—Spheroid.

*Shape* (*cross-section*).—Spheroid.

*Apex*.—Convex.

*Base*.—Truncate.

*Harvest*.—Date of first pick: early November. Date of last pick: Mid-January.

*Fruit stem*.—Length: 10 mm on average. Diameter: 2 mm on average. Color RHS: RHS 138A (Green Group).

*Rind*.—Adherence: Adherence between albedo (mesocarp) and flesh (endocarp) is medium. Thickness: 1 mm on average. Texture: Firm. Surface texture: Firm. Flavedo (epicarp): RHS 17B (Yellow-Orange Group). Albedo (mesocarp): RHS 11D (Yellow Group). Style end: Closed. Rind oil cell density: Approximately 100 cells/cm$^2$. Oil gland size: 0.6 mm on average.

*Flesh*.—Number of segments: 12 on average. Segment length: 59 mm on average. Segment width: 24 mm on average. Juice: Abundant. Color: RHS 14C (Yellow-Orange Group). Texture: Soft. Vesicle thickness: Thick. Length: 9 mm on average. Diameter: 2 mm on average.

*Juice quality*.—Brix: 9.54-12.2. Acidity (average): 0.58-0.69. Ratio: 15.40-19.06. Juice color: RHS 14C (Yellow-Orange Group). Juice color index: 31.8-36.6. Lb solid/box: Up to 5.86 from trees with HLB. Juice quality data: See Tables 1-3 below.

*Seeds*.—1-3 seeds per fruit, with an average of 2.8.

Resistance to disease: No difference observed from standard 'Hamlin'.

Data:

TABLE 1

New cultivar 'N14-10' reliably repeated for high brix (original pre-HLB data).

| Year | Number 'Hamlin' clones evaluated | 'N14-10' Rank | 'N14-10' Brix | 'N14-10' Acid | 'N14-10' Ratio |
|---|---|---|---|---|---|
| 1996 | 97 | 1 | 10.60 | 0.69 | 15.40 |
| 1997 | 102 | 12 | 11.00 | 0.65 | 16.90 |
| 1998 | 102 | 5 | 12.20 | 0.55 | 22.20 |
| 2002 | 90 | 1 | 11.99 | 0.63 | 19.03 |

Table 1. New cultivar 'N14-10' reliably repeated for high brix (original pre-HLB data).

TABLE 2

1999 Pilot Plant Fruit Quality data from 'Hamlin' somaclones selected for higher juice quality and/or color scores (harvest data Dec. 10, 1999).

| Clone | Brix | Acid | Ratio | Color |
|---|---|---|---|---|
| 'N14-35' | 9.5 | 0.73 | 13.0 | 37.4 |
| 'N13-32' | 8.9 | 0.75 | 11.9 | 36.7 |
| 'N14-30' | 9.4 | 0.69 | 13.6 | 36.7 |
| 'N13-29' | 8.3 | 0.59 | 14.1 | 36.6 |
| 'N14-10' | 10.4 | 0.66 | 15.8 | 36.6 |
| 'N15-26' | 10.5 | 0.69 | 15.2 | 36.5 |
| 'N16-30' | 9.5 | 0.73 | 13.0 | 36.5 |
| 'Hamlin' control | 9.7 | 0.60 | 16.9 | 34.5 |

Table 2. 1999 Pilot Plant Fruit Quality data from 'Hamlin' somaclones selected for higher juice quality and/or color scores (harvest data Dec. 10, 1999).

TABLE 3

Pilot Plant Fruit Quality Data comparing fruit of the new cultivar 'N14-10' with a previously released somaclone of 'Hamlin', 'N13-32'.

| Sample ID | Variety | No. Boxes | Wt. Sample (lbs.) | Wt. Juice (lbs.) | Lbs. Juice/Box | % Acid |
|---|---|---|---|---|---|---|
| N13-32 TP | HAMLI | 1 | 23.18 | 12.15 | 47.174 | 0.62 |
| N14-10 TP | HAMLI | 1 | 17.29 | 9.04 | 47.056 | 0.62 |

| Sample ID | Total ° Brix | Ratio | Bin No. | Lbs. Solids/Box | Juice Color |
|---|---|---|---|---|---|
| N13-32 TP | 9.71 | 15.66 | 74 | 4.5806 | 30.5 |
| N14-10 TP | 11.82 | 19.06 | 59 | 5.5620 | 31.8 |

Fruit data were from trees with HLB for four or more years planted at Hidden Golf Trailer Park Grove. Fruit was harvested in the first week of December 2022.

Table 3. Pilot Plant Fruit Quality Data comparing fruit of the new cultivar 'N14-10' with a previously released somaclone of 'Hamlin', 'N13-32'. Fruit data were from trees with HLB for four or more years planted at Hidden Golf Trailer Park Grove. Fruit was harvested in the first week of December 2022.

The invention claimed is:

1. A new and distinct sweet orange plant named 'N14-10' as illustrated and described herein.

* * * * *